United States Patent [19]

Martella et al.

[11] Patent Number: 5,262,508

[45] Date of Patent: Nov. 16, 1993

[54] PROCESS FOR PREPARING ALKYL PHENOL-SULFUR CONDENSATE LUBRICATING OIL ADDITIVES

[75] Inventors: David J. Martella, Princeton; John J. Jaruzelski, Westfield; Frank J. Chen, Edison, all of N.J.

[73] Assignee: Exxon Chemical Patents Inc., Linden, N.J.

[21] Appl. No.: 930,134

[22] Filed: Aug. 13, 1992

Related U.S. Application Data

[63] Continuation of Ser. No. 595,229, Oct. 10, 1990, abandoned.

[51] Int. Cl.$^5$ .............. C08G 59/00; C08G 63/78; C08G 65/38; C10M 105/08
[52] U.S. Cl. .................. 528/86; 252/42.7; 252/45; 252/48.2; 252/48.8; 252/49; 252/49.5; 528/205; 528/212; 528/214; 528/215
[58] Field of Search ............ 252/42.7, 45, 48.2, 252/48.8, 49, 49.5; 528/86, 205, 212, 214, 215

[56] References Cited

U.S. PATENT DOCUMENTS

| | | | |
|---|---|---|---|
| 1,969,324 | 8/1934 | Poulter | 61/63 |
| 2,062,672 | 12/1936 | Mastenbrook | 137/103 |
| 2,174,248 | 9/1939 | Mikeska et al. | 87/9 |
| 2,198,828 | 4/1940 | Lieber et al. | 87/9 |
| 2,209,463 | 7/1940 | Lieber et al. | 23/250 |
| 2,789,143 | 4/1957 | Arnold et al. | |
| 3,060,121 | 10/1962 | Orloff et al. | 252/48.2 |
| 3,312,621 | 4/1967 | Brownawell et al. | 252/59 |
| 3,629,225 | 12/1971 | Allphin et al. | |
| 3,630,905 | 12/1971 | Sorgo | |
| 3,668,125 | 6/1972 | Anderson | 252/59 |
| 3,763,044 | 10/1973 | Anderson | 252/59 |
| 3,778,375 | 12/1973 | Braid et al. | 252/49.9 |
| 3,779,928 | 12/1973 | Schlicht | 252/75 |
| 3,795,615 | 3/1974 | Pappas et al. | 252/59 |
| 3,835,053 | 9/1974 | Meier et al. | 252/59 |
| 3,838,049 | 9/1974 | Souillard et al. | 252/32.7 E |
| 3,852,205 | 12/1974 | Kablaoui et al. | 252/47.5 |
| 3,879,306 | 4/1975 | Kablaoui et al. | 252/51.5 A |
| 3,932,290 | 1/1976 | Koch et al. | 252/49.8 |

(List continued on next page.)

FOREIGN PATENT DOCUMENTS

| | | |
|---|---|---|
| 0249415 | 12/1987 | European Pat. Off. |
| 0311450 | 4/1989 | European Pat. Off. |
| 1498053 | 10/1967 | France |
| 2370020 | 6/1978 | France |

(List continued on next page.)

OTHER PUBLICATIONS

"Alkylation of Phenols", in *Kirk Othmer Encyclopedia of Chemical Technology*, 2nd Edition, vol. 1, pp. 894–895, INterscience Publishers, Division of John Wiley and Company, New York, 1963.

*Primary Examiner*—John Kight, III
*Assistant Examiner*—T. Mosley
*Attorney, Agent, or Firm*—V. T. White

[57] ABSTRACT

Additives for improving the low temperature flow properties and oxidative stability of hydrocarbon oils are disclosed, which comprise the alkylation of a phenol in the presence of a dipolar aprotic cosolvent to produce an essentially linear alkylated phenol which is condensated with a sulphurizing agent to produce the low temperature flow improver wherein:

(a) the polymer composition has a number average molecular weight of at least about 3,000 and a molecular weight distribution of at least about 1.5;

(b) in the alkylated phenol reactant the alkyl groups (i) are essentially linear; (ii) have between 6 and 50 carbon atoms; and (iii) have an average number of carbon atoms between about 12 and 26; and (c) not more than about 10 mole percent of the alkyl groups on the alkylated phenol have less than 12 carbon atoms and not more than about 10 mole percent of the alkyl groups on the alkylated phenol have more than 26 carbon atoms. The additives may also be produced in a branched backbone form in which monomer reactants are copolymerized with certain tri- or tetrafunctional comonomers. Blends of these additives with various hydrocarbon oils, and particularly various middle distillates and lubricating oil compositions, whose low temperature flow properties and oxidative stability are significantly improved thereby, are also disclosed.

23 Claims, No Drawings

U.S. PATENT DOCUMENTS

| | | | |
|---|---|---|---|
| 3,933,659 | 1/1976 | Lyle et al. | 252/32.7 E |
| 3,951,830 | 4/1976 | Karn | 252/42.7 |
| 3,965,019 | 6/1976 | St. Clair et al. | 252/59 |
| 3,986,981 | 10/1976 | Lyons | 252/404 |
| 4,014,663 | 3/1977 | Feldman et al. | 44/71 |
| 4,028,258 | 6/1977 | Kablaoui et al. | 252/46.7 |
| 4,068,056 | 1/1978 | Engel et al. | 526/49 |
| 4,068,058 | 12/1981 | Braid | 252/48.2 |
| 4,089,794 | 5/1978 | Engel et al. | 252/51.5 A |
| 4,105,571 | 8/1978 | Shaub et al. | 252/32.7 E |
| 4,137,185 | 1/1979 | Gardiner et al. | 252/33 |
| 4,146,489 | 3/1979 | Stambaugh et al. | 252/50 |
| 4,149,984 | 4/1979 | Wenzel et al. | 252/51.5 A |
| 4,160,739 | 7/1979 | Stambaugh et al. | 252/34 |
| 4,176,074 | 11/1979 | Coupland et al. | 252/32.7 E |
| 4,224,415 | 9/1980 | Meitzner et al. | 521/38 |
| 4,283,573 | 8/1981 | Young | 568/794 |
| 4,305,832 | 8/1982 | Gutierrez et al. | 252/33.6 |
| 4,358,565 | 11/1982 | Eckert | 525/280 |
| 4,446,039 | 5/1984 | Pindar et al. | 252/52 R |
| 4,557,849 | 12/1985 | Eckert | 252/51.5 R |
| 4,564,460 | 1/1986 | Dorer, Jr. et al. | 252/73 |
| 4,708,809 | 11/1987 | Davis | 252/33.4 |
| 4,891,465 | 1/1990 | Taniguchi et al. | 585/463 |

FOREIGN PATENT DOCUMENTS

| | | |
|---|---|---|
| WO88/03133 | 5/1988 | PCT Int'l Appl. . |
| 988800 | 1/1983 | U.S.S.R. . |
| 1167427 | 10/1969 | United Kingdom . |
| 1173975 | 12/1969 | United Kingdom . |
| 2062672A | 5/1981 | United Kingdom . |

PROCESS FOR PREPARING ALKYL PHENOL-SULFUR CONDENSATE LUBRICATING OIL ADDITIVES

This is a continuation of U.S. Ser. No. 595,229, filed Oct. 10, 1990, now abandoned.

FIELD OF THE INVENTION

The present invention relates to multi-functional additives for improving both the low temperature flow properties and the oxidation stability of hydrocarbon oils. More particularly, the present invention relates to an improved process for preparing additives for improving the low temperature flow properties and oxidation stability of various hydrocarbon oil compositions.

BACKGROUND OF THE INVENTION

A large variety of additives for improving various properties in hydrocarbon oil compositions are well known, and in fact a large number of these compositions are being used on a commercial level. The various additives are used for a variety of purposes, some of which relate to improving the low temperature (i.e., less than about 30° F.) flow properties of various types of hydrocarbon oils, including both lubricating oil fractions and other oil fractions including heating oils, diesel oils, middle distillates, and the like, and others of which relate to improving the oxidation stability of these various types of hydrocarbon oils. These flow improvers generally modify the wax crystals in both lubricating oils and other hydrocarbon fractions and crudes so as to impart low temperature handling, pumpability, and/or vehicle operability thereto. These parameters are generally measured by a variety of tests, including pour point, cloud point, mini-rotary viscometry (MRV) and others. Those other additives are used primarily for imparting anti-oxidant properties to these hydrocarbon fractions, including lubricating oil fractions.

Cloud point (ASTM D 2500) is the temperature at which wax crystals first appear as a haze in a hydrocarbon oil upon cooling. Such wax crystals typically have the highest molecular weight of the waxes in the hydrocarbon oil and therefore the lowest solubility. The cloud point of a hydrocarbon oil reflects the temperature at which problems in filtering the oil are encountered. However, the cloud point of a lubricating oil (as opposed to a fuel oil) is of less significance than is its pour point because the filters typically encountered by a lubricating oil (e.g., combustion engine oil filters) have a relatively large pore size, and filter plugging is therefore less of a problem in these environments.

Pour point is the lowest temperature at which a hydrocarbon oil will pour or flow when chilled, without disturbance, under specified conditions. Pour point problems arise through the formation of solid or semi-solid waxy particles in a hydrocarbon oil composition under chilled conditions. Thus, as the temperature of the oil is decreased, the distribution of such oil by pumping or siphoning is rendered difficult or impossible when the temperature of this oil is around or below the pour point of the oil. Consequently, when the flow of oil cannot be maintained, equipment can fail to operate.

It has therefore been necessary to develop various additives for the purpose of influencing the cold temperature flow properties of hydrocarbon oils.

The general term "lubricating oil flow improver" (LOFI) covers all those additives which modify the size, number, and growth of wax crystals in lube oils in such a way as to impart improved low temperature handling, pumpability, and/or vehicle operability as measured by such tests as pour point, cloud point, and mini rotary viscometry (MRV). The majority of lubricating oil flow improvers are polymers or contain polymers. These polymers are generally of two types, either backbone or sidechain.

The backbone variety, such as the ethylene-vinyl acetates (EVA), have various lengths of methylene segments randomly distributed in the backbone of the polymer, which associate or cocrystallize with the wax crystals inhibiting further crystal growth due to branches and noncrystallizable segments in the polymer.

The sidechain-type polymers, which are the predominant variety used as LOFIs, have methylene segments as the side chains, preferably as straight side chains. These polymers work similarly to the backbone type except the side chains have been found more effective in treating isoparaffins as well as n-paraffins found in lube oils. More specifically, LOFIs are typically derived from unsaturated carboxylic acids or anhydrides which are esterified to provide pendent ester groups derived from a mixture of alcohols. Most current commercial additives of this type thus require the use of relatively expensive alcohols for their production. Representative examples of this type of side chain LOFI include dialkyl fumarate/vinyl acetate copolymers and esterified styrene/maleic anhydride copolymers.

It would be extremely advantageous if additives could be developed which rely on less expensive olefins rather than alcohols in the synthesis of low temperature flow improvers without sacrificing the properties of conventional alcohol-based LOFIs. Several commercially unsuccessful attempts have been made in the past using alkylated phenol formaldehyde condensates.

One additive composition which has been disclosed as a pour depressant for fuels and crude oils is set forth in British Patent No. 1,173,975. The additive disclosed in this patent is a phenol-aldehyde (preferably formaldehyde) polymer in which the phenol has an R - or RCO - substituent in which R is hydrocarbyl or substituted hydrocarbyl. R is further said to contain from 18 to 30 carbon atoms, and is preferably a straight chain alkyl group. The specific examples in this patent which use olefins to provide these R groups include various internal olefins, and there is no specific disclosure regarding the advantages of using terminal olefins therein. Another patent, British Patent No. 1,167,427, discloses the use of esters of such phenolaldehyde polymers for pour point reduction of fuel oils. In both of these British patents, the oils to be treated are said to have a maximum viscosity of about 1500 cSt at 100° F., and neither recognizes the significance of utilizing specific alpha-olefins and mixtures thereof to produce these condensation products, or the advantages of imparting essential linearity to the olefin derived side chains.

Another class of such additives are essentially known as anti-oxidants or oxidation stabilizers. It is thus known that a number of phenolic and sulfur-containing compounds possess anti-oxidant properties in connection with various organic materials which are subject to oxidative decomposition in the presence of air, oxygen or ozone. These include, for example, U.S. Pat. No. 3,060,121. In this patent compounds have the general formula

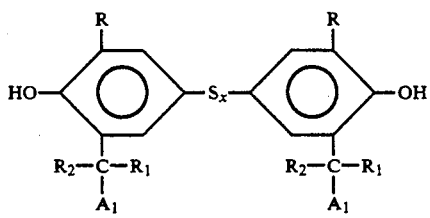

in which R, in its broadest sense, contains from 1 to 22 carbon atoms, $R_1$ and $R_2$ are up to 3 carbon atoms, A1 is up to 10 carbon atoms, x can be 3, and the maximum molecular weight under these conditions would thus be 1,346. These compounds are disclosed as anti-oxidants for certain organic materials. However, the compounds disclosed in this patent have relatively low molecular weights, again generally not more than about 1,350 as set forth above.

U.S. Pat. No. 3,986,981 discloses yet another class of anti-oxidants in this case comprising bis-phenolic polymers in which the repeating units can include compounds of the formula

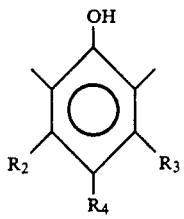

in which the $R_{2-4}$ radicals can comprise alkyl groups of from 1 to 8 carbon atoms, connected by sulfur methylene or butylidene bridging groups. Again, however, the compounds in question are of relatively low molecular weights.

Similarly, U.S. Pat. No. 3,951,830 discloses lubricant additives particularly useful as oxidation inhibitors comprising sulfur and methylene-bridged polyphenol compositions which are produced from reacting phenol with formaldehyde and subsequently sulfurizing the methylene-bridged intermediate, or as an alternative sulfurizing the phenol and then reacting same with formaldehyde. The product of same is believed to be a sulfur and methylene-bridged polyphenol composition, in which the phenol can be substituted with aliphatic or cycloaliphatic radicals of at least 6 carbon atoms and up to as many as 7,000 carbon atoms. However, all the examples in this patent use branched olefins such as polyisobutylene substituted phenols therein.

U.S. Pat. No. 4,446,039 discloses yet another additive for fuels and lubricants which, in this case, is prepared by reacting aromatic compounds, such as phenol or substituted phenol including alkyl groups of at least 50 carbon atoms, with an aldehyde, such as formaldehyde, and a non-amino hydrogen, active hydrogen compound, such as phenol, optionally along with an aliphatic alkylating agent of at least 30 carbon atoms. This patent also discloses that sulfurized additive compositions thereof can also be used as lubricant additives and fuel oil additives. It does not disclose the use of alpha-olefins of less than 50 carbon atoms for the alkylation of phenol.

Another additive for improving the various cold flow characteristics of hydrocarbon fuel compositions is in U.S. Pat. No. 4,564,460. In this patent the additives are broadly disclosed as including either an oil soluble ethylene backbone polymer or various hydrocarbyl-substituted phenols as a first component and various reaction products of hydrocarbyl-substituted carboxylic acylating agents and amines and/or alcohols. The hydrocarbyl-substituted phenol constituents of this overall additive are also broadly described, and they can include repeating aromatic moieties, such as those shown in column 14 thereof, in which the R* groups include substantially saturated monovalent hydrocarbon-based polymers of at least about 30 aliphatic carbon atoms or hydrocarbyl groups of from 8 to 30 carbon atoms. These, in turn, can be provided by internal olefins or alpha-olefins, and can be either straight or branched. Furthermore, at column 14, lines 1–40 of the patent the phenol compounds are disclosed as including various bridging compounds, including -S- (line 36). Notwithstanding the extremely broad disclosure of this patent, not a single working example is provided therein which makes or tests any hydrocarbyl substituted phenol or aldehyde condensation product thereof.

British Patent No. 2,062,672 discloses another such additive, in this case including a sulfurized alkyl phenol and a carboxylic dispersant. The alkyl phenols disclosed in this patent can include alkyl radicals of up to 1000 carbon atoms, but the disclosure also mentions the use of methylene-bridged alkyl phenols prepared by the reaction of the alkyl phenol and formaldehyde.

Canadian Patent No. 1,192,539 discloses yet another alkyl-phenol-containing lubricant additive. In this case the lubricant is designed for two-cycle engines and the phenolic compound includes a hydrocarbyl group of an average of at least ten aliphatic carbon atoms, and preferably containing at least 30 and up to 400 aliphatic carbon atoms (page 11, lines 13–17). Furthermore, the disclosure states that the aromatic ring can be a linked polynuclear aromatic moiety, which can also include other substituents, and which can be linked by a number of groups, including sulfide linkages (page 6, lines 1–8). Once again in this case the disclosure is very broad, and includes innumerable variations on the alkyl phenol component.

There are also a number of patents which disclose other alkyl phenol polysulfides, primarily di-sulfides, as additives to mineral oils to improve properties including high temperature stability thereof. These include U.S. Pat. No. 2,174,248 which teaches the use of alkyl phenols produced from olefins of from 2 to 8 carbon atoms with the sulfur compound to produce the di-sulfide. Also, U.S. Pat. Nos. 2,198,828 and 2,209,463 have similar disclosures in this regard.

British Patent No. 2,062,672 discloses another such additive, in this case including a sulfurized alkyl phenol and a carboxylic dispersant. The alkyl phenols disclosed in this patent can include alkyl radicals of up to 100 carbon atoms, but the disclosure also mentions the use of methylene-bridged or sulfur bridged alkyl phenols prepared by the reaction of the alkyl phenol and formaldehyde or a sulfurizing agent.

U.S. Pat. No. 3,629,225 also discloses sulfurized alkyl phenols of limited size (up to three repeating units), and U.S. Pat. No. 4,305,832 discloses a sulfurized phenol composition as set forth in column 1 thereof in which the phenols include an alkyl group having from 1 to 18 carbon atoms, and the overall compositions again have a limited molecular weight with up to four repeating units therein.

Irrespective of all of the above, and the large number of additive compositions which have previously been proposed and utilized for altering both the flow properties and the oxidative stability of hydrocarbon oils and lubricating oil compositions, the search has continued for additional additive compositions which can improve both the flow characteristics and the oxidative stability of these various hydrocarbon compositions, and which can also be easily produced on an economical basis.

Commonly assigned U.S. Pat. Nos. 5,039,437 and 4,976,882, both filed on Oct. 8, 1987 by some of the same inventors herein are directed to alkyl phenol-aldehyde condensates and sulfur bridged alkyl phenols condensates respectively and are incorporated herein by references.

SUMMARY OF THE INVENTION

The present invention, provides a polymer composition capable of improving both the low temperature flow properties and the oxidation stability of hydrocarbon oils wherein the condensation reaction product is prepared from linear alkylated phenol prepared by conducting the alkylation of the phenol in the presence of a dipolar aprotic cosolvent. The condensation reaction products of reactants comprising alkylated phenol prepared by the method of the invention, comprising at least 80 mole percent of difunctional alkylated phenol, and a sulfurizing agent wherein:

(a) the polymer composition has a number average molecular weight of at least about 3,000 and a molecular weight distribution of at least about 1.5;

(b) in the alkylated phenol reactant the alkyl groups (i) are essentially linear; (ii) have between 6 and 50 carbon atoms; and (iii) have an average number of carbon atoms between about 12 and 26; and (c) not more than about 10 mole percent of the alkyl groups on the alkylated phenol have less than 12 carbon atoms and not more than about 10 mole percent of the alkyl groups on the alkylated phenol have more than 26 carbon atoms.

In a preferred embodiment, the polymeric composition can be represented by the formula:

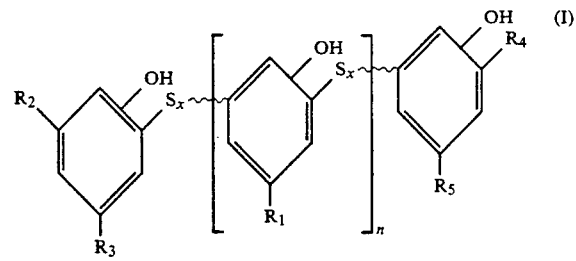

(I)

wherein (a) x comprises an integer from 1 to about 8; (b) $R_1$ represents alkyl derived from linear alpha-olefins having from 6 to 50 carbon atoms; (c) $R_2$, $R_3$, $R_4$ and $R_5$ represent hydrogen or alkyl derived from linear alpha-olefins having from 6 to 50 carbon atoms, provided that at least one of $R_2$ and $R_3$ and at least one of $R_4$ and $R_5$ are alkyl; (d) in the alkyl groups constituting $R_1$ to $R_5$; (i) the average number of carbon atoms is between about 12 and 26; (ii) not more than about 10 mole percent of said alkyl groups have less than 12 carbon atoms and not more than about 10 mole percent of said alkyl groups have more than 26 carbon atoms; and (iii) the alkyl groups are essentially linear; (e) n is a number of at least about 3; and (f) the polymer has a number average molecular weight of at least about 4,500 and a molecular weight distribution of at least about 1.5.

In another aspect of the present invention linear backbones are crosslinked during formation with comonomer, which preferably can be either a trifunctional comonomer having the formula:

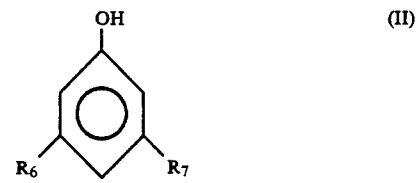

(II)

wherein $R_6$ and $R_7$ can be hydrogen, alkyl, aryl, alkoxy, aryloxy, alkyl mercapto, or halogen; or a tetrafunctional comonomer having the formula:

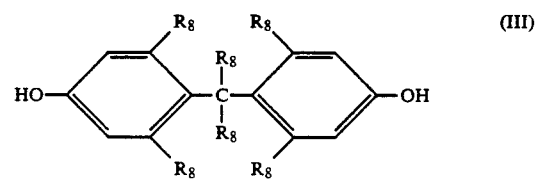

(III)

wherein $R_8$ can be hydrogen, alkyl, aryl, alkoxy, aryloxy, alkyl mercapto, or halogen.

In accordance with another aspect of the present invention, polymeric additives are provided by reacting alkylated phenol prepared as disclosed herein, represented by the formula:

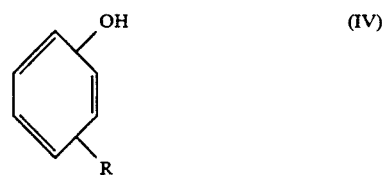

(IV)

wherein R represents essentially linear alkyl having from 6 to 50 carbon atoms in which the average number of such carbon atoms in all of the alkyl groups is between about 16 and 22, wherein not more than about 10 mole % of the alkyl groups have less than 16 carbon atoms and not more than about 10 mole % of the alkyl groups have more than 22 carbon atoms, with a sulfurizing agent selected from the group consisting of elemental sulfur and sulfur-containing compounds having the formula $S_xCl_2$, wherein x is 1 or 2, and optionally comonomer selected from formulas (II) and (III) above.

In accordance with another aspect of the present invention, a method for preparing these polymeric compositions is provided.

In accordance with the present invention, the condensation step is conducted in the presence of the trifunctional or tetrafunctional comonomer components discussed above.

DETAILED DESCRIPTION OF THE INVENTION

The additives of the present invention comprise fuel oil and lubricating oil flow improvers which are effective and employed for modification of the size, number, and growth of wax crystals in various hydrocarbon oils, including fuel oils and lubricating oils, so as to impart improved low temperature flow properties to these oils, and which are also effective for inhibiting the oxidation of these hydrocarbon oils. Most particularly, when used in connection with lubricating oil compositions, these lubricating oil additives are also effective to improve the low temperature handling, pumpability, and/or vehicle operability as measured by such tests as pour point and mini-rotary viscometry (MRV), and they are effective to reduce the extent of oxidation of these lubricating oils with time. When used in connection with fuels, such as middle distillate petroleum fuels, as well as diesel fuels, heating oils and the like, these fuel oil flow improvers are also effective to improve the low temperature handling characteristics thereof, as most particularly measured by such tests as cloud point and pour point tests.

The additive compositions of the present invention are prepared by the alkylation of phenol conducted in the presence of at least one dipolar aprotic cosolvent to minimize the amount of rearrangement and to import essential linearity to the alkyl group of the alkylate, followed by condensation with a sulfurizing agent so as to produce polymers having certain specified molecular weights. More particularly, the use of the specific linear alpha-olefins which are set forth below in the manner described results in superior lubricating oil and fuel oil flow improvers relative to the alkyl phenol-sulfur condensates in the prior art, and which also exhibit significant anti-oxidant properties. As will be demonstrated, these particular polymers are particularly and unexpectedly superior in terms of their ability to co-crystalize with the wax crystals in these hydrocarbon oils which again have multi-functional characteristics.

The particular alkyl phenol-sulfur condensates which form the basic polymers of the present invention are generally produced by an initial alkylation step of the invention followed by condensation with the sulfurizing agent.

Alkylation of the phenol is initially conducted with a linear alpha-olefin or blend of linear alpha-olefins which are terminal olefins, as contrasted to internal olefins. In this manner, it is possible to produce final polymers in which the alkyl group attached to the benzene ring is essentially linear. By "essentially linear" is meant greater than 35, preferably at least 40, and most preferably at least 50 mole percent of the alkyl groups derived from the olefin alkylating agent (exclusive of the alkyl groups of any optional tri-or tetrafunctional component described hereinafter for molecular weight enhancement) and attached to the aromatic ring of the phenol group in the alkylated product is linear, except for a methyl group pendant from the carbon attached to that aromatic ring. More specifically, since terminal alpha-olefins are employed for the alkylation of phenol in accordance herewith, the terminal olefins will attach to the aromatic ring at the beta carbon thereof, thereby leaving the alpha carbon as a methyl group pendant from the beta carbon of the original olefin. Thus, expressed differently, "essentially linear" means greater than 35 mole percent of the alkyl groups of the alkylated phenol are alpha methyl substituted linear alkyl. The primary alkyl phenol product desired from this alkylation step (after rearrangement as discussed hereinafter) will be linear to at least that extent.

More specifically, the initial alkylation step itself is an exothermic reaction of phenol with these particular linear terminal alpha-olefins. This reaction can thus be shown as follows:

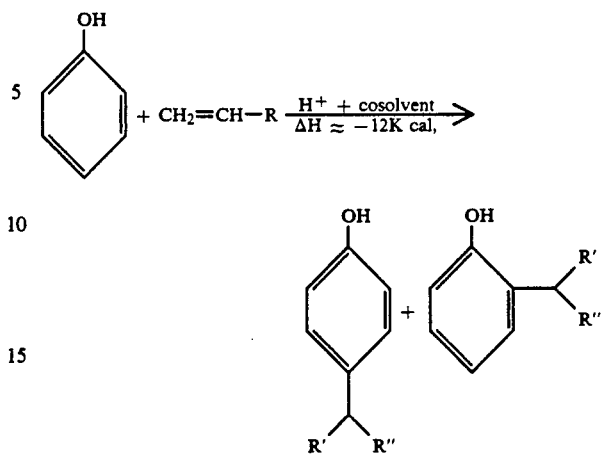

and in which R is linear alkyl, and R' and R" are linear alkyl groups derived in whole or in part from R. This exothermic reaction is thus a simple cationic reaction resulting in a somewhat complex product. In the ideal reaction the olefin forms a carbonium ion species as a result of the presence of acidic conditions and temperatures. This cation can then readily react with phenol at either the ortho or para positions. Without rearrangement, the carbonium ion species will attach to the aromatic ring at the beta carbon of the olefin, and R' will thus constitute a pendant methyl group derived from the alpha carbon of the original olefin, with R" constituting the remainder of the linear alkyl chain originally defined by R. In reality, however, many side reactions are possible. Thus, the cation can revert back to the olefin or rearrange further down the linear chain, thereby producing attachment to the aromatic ring at a more internal carbon atom, and causing the length of R' to increase, and R" to decrease in length correspondingly. It has been found that if these rearrangements are too extensive, they will lead to the production of inferior products which would not suitably interact with the wax crystals of the lubricating oil or fuel oil to which they are eventually added.

It is therefore critical to the present invention to minimize these rearrangements and to maximize the attachment of the alkyl groups at the 2-position (i.e., beta carbon of the original linear olefin). The instant invention presents a novel method of producing alkyl phenols having essentially linear alkyl substituted groups. The present invention describes a method to produce alkyl phenols with less rearrangement, and thereby an alkyl phenol-sulfur condensate with greater pour point depressancy. The method involves conducting the alkylation of phenol desirably in the presence of at least one dipolar aprotic cosolvent. The cosolvent of the invention should have a dielectric constant of greater than about 10 and preferably greater than about 20 and desirably from 20 to about 50. Typical examples of suitable cosolvents are 1,2-dichloroethane (e=10.4), hexamethylphosphoramide (e=21), N-methyl-pyrrolidone (e=32), nitrobenzene (e=35), nitromethane (e=36), N-N-dimethylformamide (e=37), acetonitrile (e=36), sulfolane (e=44) and dimethyl sulfoxide (e=47). The use of these dipolar aprotic cosolvents in the alkylation reaction significantly minimizes the amount of rearrangement and maximizes the attachment of the alkyl groups at the 2-position which thereby increases the pour point depressancy of the resulting alkyl phenol-sulfur condensates. The amount of solvent used is not critical and it would be within the knowledge of one skilled in the art to determine suitable amount without undue experimentation. Generally, amounts of above 50 wt. % of the reactant is considered suitable. Amounts, however, greatly in excess of that stated above would not be considered detrimental, but may present problems with removal and would not be cost effective for the process. The minimum amount would be that necessary to produce the desired product.

Other methods for minimizing such rearrangement are disclosed in U.S. Pat. Nos. 4,976,882 and 5,039,437 referred to above and incorporated herein by reference. The methods disclosed in these pending applications are preferably used in combination with the instant invention. One method, for instance, comprises carrying out the alkylation process at lower reaction temperature as opposed to elevated reaction temperatures. Therefore, the alkylation process itself can generally be conducted at temperatures of at or below about 100° C., preferably at or below 90.C, e.g., typically between about 50° and 100° C., and preferably between about 50° and 90° C., to minimize rearrangement.

It has also been observed in the applications referenced above, that rearrangment is more likely to occur at the para position than the ortho position. This is probably a result of a steric factor which permits greater accommodation of rearrangement at the para position to the hydroxyl group. Accordingly, the definition of "essentially linear" accounts for, and expresses the permissible limits of, the above-discussed autogenous rearrangement in forming the alkylate product. In short, "essentially linear" expresses the maximum degree of acceptable branching in the alkylate product which can be tolerated when starting with linear alpha-olefins. The degree of rearrangement is typically determined by $^1$H-NMR and/or by high pressure liquid chromatography.

Another critical aspect in the preparation was found to be the carbon number and carbon number distribution of olefins employed for alkylation.

The particular linear alpha-olefins used in connection with the alkylation step of the present invention are, as indicated above, crucial to the manufacture of the proper additives for use herein. In particular, these linear alpha-olefins have the formula $CH_2=CH-R$, in which R is straight chain alkyl having between about 4 and about 48 carbon atoms, and in which the specific alpha-olefin or mixture of alpha-olefins used for this alkylation has an average carbon number (on a molar basis for mixtures of olefins) of between about 12 and 26 (e.g. 14 and 24), preferably between about 16 and 22 (e.g., 17 and 21, or 16 and 19), and most preferably between about 18 and 20.

Moreover, the olefin mixture as was disclosed, should not contain more than about 10 mole percent, preferably not more than about 5 mole percent, and most preferably not more than about 2 mole percent of alpha-olefins having independently: (a) less than about 12, preferably not less than about 14, and most preferably not less than about 16 carbon atoms; and (b) not more than about 26, preferably not more than about 24, and most preferably not more than about 22 carbon atoms. These proportional requirements are thereby incorporated into, and embodied in, the final condensate polymer.

The particular average carbon number range which was most depended upon the ultimate environment of the alkyl phenol condensate which was produced thereby. That is, when used in connection with fuel oil formulations, additives made in accordance with the present invention will preferably utilize a slightly lower average carbon number for these R groups.

More particularly, it was found that in connection with such fuel oils, including diesel fuels and heating oils, to maximize cloud point reduction an average carbon number of about $C_{18}$ was most desired, while to maximize pour point reduction an average carbon number of about $C_{16}$ was most desired.

On the other hand, in connection with lubricating oil compositions the average carbon number for maximizing pour point reduction was an average carbon content of from about $C_{18}$ to $C_{20}$.

Moreover, within each class of hydrocarbon oils, i.e., fuel or lubricating oil, each specific hydrocarbon oil can be associated with an optimum average carbon number for the R group (also referred to herein as the alkylate average carbon number) to achieve maximum cloud point or pour point depressancy relative to the base oil without any additive. Optimum pour depressancy will typically be achieved by an average carbon number that is lower than that needed to achieve optimum cloud pour point depressancy for a given hydrocarbon oil.

It was further found that while the molecular weight and molecular weight distribution ($M_w/M_n$) of the condensate polymer, degree of branching, and concentration of the condensation polymer in the hydrocarbon oil all affect, and are important for achieving low temperature flow performance, the two most dominant factors are the optimum alkylate average carbon number and the essential linearity of the alkyl group.

It was also believed that in any given situation the use of a range of alpha-olefins surrounding the optimum average carbon number was superior to the use of a single alpha-olefin having that number of carbon atoms. In any event, the most preferred alpha-olefins for use herein will thus include 1-hexadecene, 1-octadecene, 1-eicosene, 1-docosene, 1-tetracosene, and mixtures thereof.

A further important factor in conducting the alkylation reaction was the minimization of monofunctional alkylation product (e.g., most dialkylate products), and the maximization of difunctional alkylate products (e.g., mono alkylates) in the phenol alkylation reaction. As discussed hereinafter, the final alkyl phenol sulfur condensation product is synthesized to possess certain minimum requirements in terms of molecular weight and molecular weight distribution. If the alkylated phenol product mixture employed for condensation contains too much monofunctional dialkylate, then the final condensation polymer will not meet such requirements. This stems from the fact that when a second alkyl group attaches to the phenol to yield a 2,4- or 2,6-dialkyl phenol, it results in a monofunctional dialkylate molecule which, if reacted with a growing polymer chain, would terminate chain growth in the following manner:

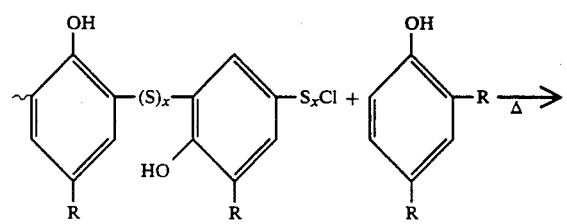

-continued .

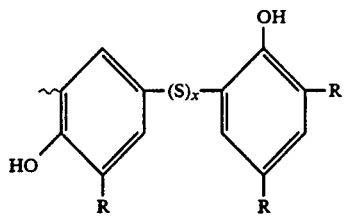

More specifically, the functionality of the alkylated-phenol reaction product expresses the number of available reactable sites, which remain on the alkylated phenol after alkylation, that can participate in the polymerization reaction through propagation of a growing polymer chain. The only freely reactable sites on an unsubstituted phenol molecule for purposes of polymerization are the 2-, 4-, and 6- carbons of the phenol aromatic ring. Thus, unsubstituted phenol is a trifunctional molecule. If monoalkylation occurs at only one of the 2-, 4-, or 6-positions, the resulting mono-alkylate is said to be difunctional, since one of the reactable sites has been eliminated through substitution of an alkyl group thereon. Similarly, the substitution of alkyl groups at any two of the 2-, 4-, or 6- carbons of the phenol molecule through dialkylation will result in the formation of a monofunctional dialkylate product. Thus, 2,4-dialkyl phenol and 2,6-dialkyl phenol are monofunctional dialkylates which will lead to chain termination, and thereby limit polymer molecular weights. While 2,5-dialkyl phenol and 3,5-dialkyl phenol are difunctional and trifunctional dialkyl monomers, respectively, such monomers do not normally form under typical alkylation conditions, because such formation would involve reaction at normally unreactive sites. Consequently, one seeks to minimize dialkylation generally, as most dialkylation leads to formation of monofunctional monomer. Thus, reference to dialkylation herein as being undesirable is technically a reference only to dialkylation which yields monofunctional dialkylate.

An equation relating the maximum degree of polymerization (DP) to the extent of reaction ($p$) and the functionality (f) of the reactants is referred to as the Modified Carothers Equation:

$$DP=2/(2-pf)$$

This equation can be used to show that a monofunctional dialkylate monomer severely limits the maximum degree of polymerization in the alkyl phenol-sulfur condensation reaction.

As was disclosed in U.S. Pat. Nos. 4,976,882 and 5,039,437, referenced above and incorporated herein, the use of separately synthesized tri- and tetrafunctional comonomers can be employed to increase the molecular weight of the final condensation polymer and/or to compensate for the presence of monofunctional dialkylate monomer.

Thus, the target molecular weights as disclosed was suitably achieved by controlling the amount of difunctional (e.g., monoalkylate) monomer to be typically at least about 80 mole %, and preferably at least about 85 mole and most preferably at least about 90 mole %, and typically from about 80 to about 100 mole %, preferably from about 85 to 100 mole %, and most preferably from about 90 to 100 (e.g., 95 to 100) mole %, based on the total moles of alkylate monomer in the monomer mixture intended for polymerization.

Correspondingly, the amount of monofunctional dialkylate monomer which can be tolerated will typically range from about 0 to about 20 mole %, preferably from about 0 to about 15 mole %, and most preferably from about 0 to about 10 (e.g. 0 to about 5) mole % based on the moles of monomer in the alkylate monomer mixture.

High functionality monomers, such as the tri- and tetrafunctional comonomers described hereinafter, are typically employed in collective amounts of from about 0 to about 10 mole %, preferably from about 2 to about 8 mole %, and most preferably from about 3 to about 5 mole %, based on the total moles of alkylate monomer in the alkylate monomer mixture.

One way to minimize dialkylation in attempting to meet the condensation polymer molecular weight targets specified was to employ excess phenol relative to the olefin for the alkylation reaction. Accordingly, effective molar ratios of phenol to olefin can vary typically from about 2:1 to about 10:1 (or higher), preferably from about 2:1 to about 5:1. From a process standpoint, however, too much of an excess of phenol can be disadvantageous because of the need to remove the excess phenol from alkylation product after alkylation is completed.

Thus, it was found that certain zeolite catalysts permit one to lower the phenol:olefin molar ratio to less than about 2:1, preferably between about 1.7:1 and about 1:1 and still achieve minimization of dialkylation. This low ratio extremely simplifies unreacted phenol recovery.

The alkylation reaction can generally be accomplished, within the above parameters, by a number of techniques known to those skilled in this art. One particularly suitable technique is described using the Friedel-Crafts reaction which occurs in the presence of a Lewis acid catalyst, such as boron trifluoride and its complexes with ethers, hydrogen fluoride, etc., aluminum chloride, aluminum bromide, and zinc dichloride, etc. Methods and conditions for carrying out such reactions are well known to those skilled in this art, and reference is made, for example, to the discussion in the article entitled "Alkylation of Phenols," in Kirk-Othmer Encyclopedia of Chemical Technology, 3rd Edition, Vol. 2, pp. 65–66, Interscience Publishers, Division of John Wiley and Company, New York, 1963, which is incorporated herein by reference thereto. A particularly preferred catalyst for use in such alkylation reactions is designated Amberlyst 15 by the Rohm and Haas Company. This catalyst is included among the strongly acidic macroreticular resins patented under U.S. Pat. No. 4,224,415. This resin is itself composed of long chains of polystyrene locked together by divinylbenzene crosslinks into a three-dimensional, insoluble polymeric phase called a matrix, on which are attached sulfonic acid groups (—SO$_3$H). Amberlyst 15 possesses high acidity (4.7 meq/g), high porosity (32%) and high surface area (45 m$^2$/g).

In a highly preferred method for carrying out the alkylation reaction as disclosed herein, a zeolite catalyst is employed for use in the selective production of the desired mono-alkylate. More particularly, crystalline zeolites are used which have high silica to alumina ratios and which have effective pore sizes of between about 6 and 8 Angstroms, and include a number of commercial zeolite catalysts, such a LZ-Y82 catalyst manufactured by Union Carbide Corporation. In any event, a general description of these zeolites is set forth in Young, U.S. Pat. No. 4,283,573, which is incorporated herein by reference thereto. In general, these zeolites have a crystal structure which provides access to and egress from the intracrystalline free space of the zeolites by virtue of having channels or networks of pores, the openings of which again preferably have a major dimension, or a free pore diameter, of between about 6A and about 8A. These zeolites are also characterized by pore apertures of about a size as would be provided by 12-member rings of silicon and aluminum atoms. The preferred types of zeolites for use in this invention possess a silica to alumina molar ratio of from about 3:1 to about 6:1. This ratio represents, as closely as possible, the ratio in the rigid anionic framework of the zeolite crystal. Furthermore, these preferred zeolites will have a high surface area, such as about 625 $m^2/g$. The use of these zeolite catalysts thus permits one to eliminate the expensive and difficult distillation step required to separate the mono-alkylate from the di-alkylate produced with the acid-type catalysts previously utilized.

In connection with the alkylated phenol product, the use of a linear alpha-olefin or a mixture of linear alpha-olefins gives a ratio of ortho to para attachments on the phenol of about 2:1. In contrast with the alkylated phenol product of this reaction, the use of a branched internal olefin or a mixture of branched internal olefins gives a ratio of ortho to para attachments on phenol of about 1:18. However, essentially linear alkyl groups attached either ortho or para to the hydroxy group perform equally well.

The next step in the preparation of the polymer additives using the essentially linear alkylated phenol prepared as disclosed herein is the actual polymerization or condensation reaction. The reaction itself is a condensation of the above-described alkyl phenol in the presence of a sulfurizing agent. The sulfurizing agent has been defined to be any compound or element which introduces —$(S)_x$— bridging groups between the alkylated phenol monomer groups, wherein x is a number of from 1 to about 8. Thus, the condensation reaction can be conducted with elemental sulfur or a halide thereof such as sulfur monochloride or, more preferably, sulfur dichloride. If elemental sulfur is used, this reaction is effected by heating the alkyl phenol compound at between about 50° and 250° C., and usually at least about 160° C. The use of elemental sulfur typically yielded a mixture of bridging groups —$(S)_x$— as described above. When sulfur halide was used, this reaction was effected by heating the alkyl phenol compound at between about 50 and 120° C., and usually at about 80° C. Optimally, the reaction is conducted in the presence of a suitable diluent. The diluent can generally comprise a substantially inert organic diluent such as mineral oil or an alkane, ketone, ether, ether alcohol, or the like. In any event, the reaction is conducted for a period of time sufficient to effect substantial reaction. It is generally preferred to employ between about 0.1 and 5 moles of the alkyl phenol material per equivalent of sulfurizing agent.

When elemental sulfur was used as the sulfurizing agent, it is frequently preferred to use a basic catalyst such as sodium hydroxide or an organic amine, preferably a heterocyclic amine (e.g., morpholine).

Particularly where sulfur halides are used as the sulfurizing agent, it is frequently preferred to use an acid acceptor, such as sodium hydroxide, calcium carbonate or the like, to react with the hydrogen halide evolved therein.

Pressure is not a critical factor, and can be atmospheric or below, up to 1000 psi or higher. Atmospheric pressure is preferred for convenience, and the pressure should be sufficient to maintain the reactants in the liquid phase.

The reactants, together with catalyst and any diluent which is employed, can thus be charged to a reactor and reacted under the conditions set forth above. The crude reaction product mixture can then be cooled, neutralized, water-washed to remove any catalyst, dried, and then stripped to remove excess reactant, any unreacted materials, and any diluent that may have been used.

The condensation reaction is conducted in a manner and under conditions sufficient to achieve or surpass certain minimum number average and weight average molecular weight targets. Accordingly, the condensation reaction is conducted to impart to the final polymer a number average molecular weight ($M_n$) as determined by vapor-phase osmometry of at least about 3,000 (e.g., at least about 4,000), preferably at least about 5,000, and most preferably at least about 7,000, and typically from about 3,000 to about 60,000 (e.g., 4,000 to 60,000), preferably from about 5,000 to about 30,000, most preferably from about 7,000 to about 20,000, and a weight average molecular weight (Mw) as determined by gel permeation chromatography, of at least about 4,500 (e.g., at least about 5,000), preferably at least about 6,000, and typically from about 4,500 to about 100,000, preferably from about 10,000 to about 70,000 (e.g., 6,000 to about 35,000), and most preferably from about 20,000 to about 50,000.

The maximum number and weight average molecular weights are limited only by the solubility of the condensate polymer in the particular hydrocarbon basestock in question.

It is most preferred that these polymers have a ratio of weight average molecular weight to number average molecular weight ($M_w/M_n$), commonly referred to as molecular weight distribution, of greater than about 1.5, preferably greater than about 2.0, and most preferably greater than about 2.5, and typically from about 1.5 to about 34, preferably from about 2.0 to about 24, and most preferably from about 3.0 to about 7.0. Generally, the higher the weight average molecular weight, the better suited or more effective these polymers are for improving the flow properties of various hydrocarbon oils in accordance with the present invention.

While number average molecular weight ($M_n$) can conveniently also be determined by gel permeation chromatography (GPC), it is considered that VPO techniques are more accurate, although the $M_n$ by the GPC technique will typically approximate $M_n$ by VPO within ±1000, more typically ±500.

In one embodiment, polymers or condensates which are thus produced in accordance with this process can be represented by the following formula:

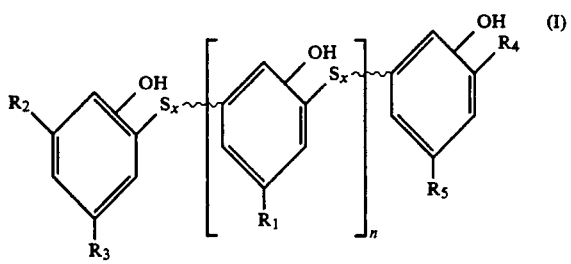

in which x is an integer of typically from 1 to about 8, preferably from about 1 to about 5, and most preferably from about 1 to about 2, $R_1$ represents attached essentially linear alkyl groups discussed above derived from the linear alpha-olefin having from about 6 to 50 carbon atoms, in which the average number of carbon atoms in all of the groups constituting $R_1$ is between about 12 and 26, preferably between about 16 and 22, and most preferably between about 18 and 20, and in which no more than about 10 mole percent of alkyl groups have less than 12 carbon atoms and no more than about 10 mole percent of alkyl groups have more than 26 carbon atoms; $R_2$, $R_3$, $R_4$ and $R_5$ independently can represent hydrogen or alkyl as described in connection with $R_1$, with the proviso that at least one of $R_2$ and $R_3$ is said alkyl and at least one of $R_4$ and $R_5$ is said alkyl. The hydroxy group of the phenol will be located on an aromatic carbon which is adjacent to a carbon on which at least one of the —$(S)_x$— groups is attached.

The value of n is subject to the number average molecular weight targets discussed above, and the minimum value thereof expressed hereinafter will consequently vary depending on the average carbon number of the olefins employed for alkylation, the average value of x, and the number of repeating units controlled by n necessary to achieve such $M_n$ values when accounting for said olefin average carbon number and the average value of x.

Accordingly, n is a number which, subject to the above constraints, will typically be at least 3 (e.g., at least 5), preferably at least 8 (e.g., at least 10), and most preferably at least 12, and can vary typically from about 5 to about 80, preferably from about 10 to about 60, and most preferably from about 15 to about 30.

As indicated above, it can be somewhat difficult to increase the molecular weights of the alkylated phenol-sulfur condensates beyond a certain level because of the propensity of dialkylate monomers to terminate chain growth.

There are yet additional methods of increasing the molecular weight of the alkylated phenol-sulfur condensate flow improvers of the present invention. In this method, the polymerization step is carried out in the additional presence of trifunctional or tetrafunctional comonomer (functionality being reactable sites) so as to produce an ultimate condensation polymer having a branched backbone rather than linear backbone as shown in formula (I) hereinabove wherein said linear backbones are crosslinked through said trifunctional and/or tetrafunctional comonomers.

In particular, a trifunctional comonomer having the following formula can be employed:

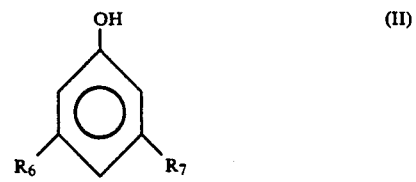

in which $R_6$ and $R_7$ can be hydrogen, alkyl, aryl, alkoxy, aryloxy, alkyl mercapto, and halogen. More particularly, it is preferred that $R_6$ and $R_7$ include branched or straight chain alkyl groups, preferably straight chain, such as $C_1$ through $C_{30}$ alkyl, preferably methyl, $C_6$ through $C_{14}$ aryl, $C_1$ through $C_{22}$ alkoxy, $C_6$ through $C_{14}$ aryloxy, $C_1$ to $C_{30}$ alkyl mercapto, and preferably halogens such as chlorine and bromine.

As discussed above, 3,5-dialkylate is difficult to achieve under normal alkylation conditions. Consequently, a variety of methods well known in the art can be employed to achieve 3,5-dialkylation. One such method involves a thallation reaction wherein, for example, 1,3-dimethyl benzene is contacted with a thallium trifluoro acetate catalyst to cause stereo specific oxidation to 3,5-dimethyl phenol.

Representative examples of trifunctional monomers include phenol, m-cresol, 3,5-xylenol, m-phenyl phenol, m-methoxyphenol, orcinol, and m-methyl mercapto phenol, while phenol is preferred.

For example, when phenol is employed as the trifunctional monomer, then a portion of the branched backbone can be represented by the following formula with an asterisk indicating the original phenol trifunctional monomer:

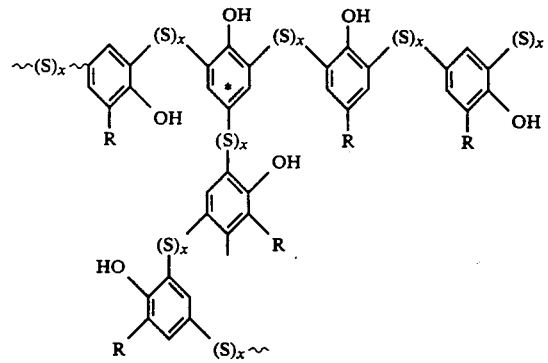

It is thus possible in this manner to produce such polymer condensates having weight average molecular weights determined by gel permeation chromatography of greater than about 10,000, preferably between about 10,000 and 100,000, and most preferably greater than about 20,000.

Even further branching is achieved with tetrafunctional monomer which can crosslink four linear backbones.

The tetrafunctional comonomers which can be used in the polymerization step of the present invention can have the formula:

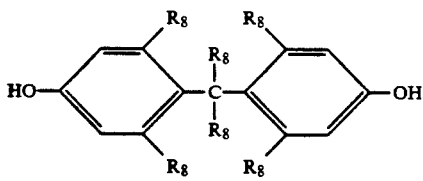

(III)

in which $R_8$ independently can be the same hydrogen, alkyl, aryl, alkoxy, aryloxy, alkyl mercapto, and halogen components discussed above in connection with the trifunctional comonomers as formula II hereof. Representative examples of suitable tetrafunctional monomers include bisphenol A, bisphenol B, methylene-4,4,-bis (3,5-dibutylphenol), methylene-4,4'-bis (3,5-dimethoxyphenol), methylene-4,4'-bis (3,5-dimethylmercapto phenol), with bisphenol A being preferred. Again, in this case it is also possible to produce such polymer condensates having weight average molecular weights determined by gel permeation chromatography of greater than about 10,000, preferably between about 10,000 and 100,000, and most preferably greater than about 20,000.

The amount of such trifunctional and/or tetrafunctional comonomer employed in the polymerization or condensation step of the present invention must, however, be limited to a certain extent. That is, the amount of comonomer present should be less than about 10 wt. % of a combination of the alkylated phenol and the sulfurizing agent, and preferably less than about 8 wt. %. It has thus been found that if too great an amount of the trifunctional and/or tetrafunctional comonomer is present, that material tends to crosslink to the extent that an insoluble mass can be formed thereby. This can be avoided, however, by using the amounts discussed above, and additionally by conducting the polymerization in the initial presence of small amounts of the trifunctional or tetrafunctional comonomer. Also, this comonomer can be continuously added during the course of polymerization, thereby becoming diluted with the polymerizing alkyl phenol composition to maintain the comonomer as dilute as possible throughout the polymerization reaction.

It is also contemplated, although less preferred, that blends of separately synthesized alkyl phenol condensates meeting the aforedescribed requirements can be employed.

For purpose of discussion, when such blends are employed, the overall alkylate average carbon number for each polymer component in the blend in which the alkylate portion thereof is derived from a single alpha-olefin, or single mixture of alpha-olefins, can also be referred to herein as the alkylate intra-molecular carbon average. However, the alkylate intra-molecular carbon average of each polymer component in the blend can then also be averaged on a molar basis to determine what is referred to herein as the alkylate inter-molecular carbon average for the blend.

It is believed that when the optimum alkylate average carbon number (i.e., intra-molecular average carbon number) has been determined for a particular hydrocarbon oil, the best low temperature performance is achieved by a single polymer which possesses this optimum average carbon number value, rather than a blend of polymers wherein each polymer component in the blend possesses a non-optimum alkylate intra-molecular carbon average, but the blend collectively possesses an alkylate inter-molecular carbon average value equal to the value of the optimum intra-molecular carbon average.

The polymer additives produced in accordance with the present invention have been found to be useful in fuel oils and lubricating oils. The normally liquid fuel oils are generally derived from petroleum sources, e.g., normally liquid petroleum distillate fuels, though they may include those produced synthetically by the Fischer-Tropsch and related processes, the processing of organic waste material or the processing of coal, lignite or shale rock. Such fuel compositions have varying boiling ranges, viscosities, cloud and pour points, etc., according to their end use as is well known to those of skill in the art. Among such fuels are those commonly known as diesel fuels, distillate fuels, heating oils, residual fuels, bunker fuels, etc., which are collectively referred to herein as fuel oils. The properties of such fuels are well known to skilled artisans as illustrated, for example, by ASTM Specification D #396-73, available from the American Society for Testing Materials, 1916 Race Street, Philadlephia, Pa. 19103.

Particularly preferred fuel oils include middle distillates boiling from about 120° to 725° F. (e.g., 375° to 725° F.), including kerosene, diesel fuels, home heating fuel oil, jet fuels, etc., and most preferably whose 20% and 90% distillation points differ by less than 212° F., and/or whose 90% to final boiling point range is between about 20° and 50° F. and/or whose final boiling point is in the range of 600 to 700° F.

The additives derived from the process of this invention find their primary utility, however, in lubricating oil compositions, which employ a base oil in which the additives are dissolved or dispersed. Such base oils may be natural or a mixture of natural and synthetic oils.

Thus, base oils suitable for use in preparing the lubricating oil compositions of the present invention include those conventionally employed as crankcase lubricating oils for spark-ignited and compression-ignited internal combustion engines, such as automobile and truck engines, marine and railroad diesel engines, and the like. Advantageous results are also achieved by employing the additives derived from the process of the present invention in base oils conventionally employed in and/or adapted for use as power transmitting fluids such as automatic transmission fluids, tractor fluids, universal tractor fluids and hydraulic fluids, heavy duty hydraulic fluids, power steering fluids and the like. Gear lubricants, industrial oils, pump oils and other lubricating oil compositions can also benefit from the incorporation therein of the additives derived from the process of the present invention.

Thus, the additives produced as disclosed herein may be suitably incorporated into mixtures of natural and synthetic base oils provided these mixtures include at least about 80 wt. % of natural base oil. Suitable synthetic base oils for use in these mixtures include alkyl esters of dicarboxylic acids, polyglycols and alcohols; polyalphaolefins, polybutenes, alkyl benzenes, organic esters of phosphoric acids, polysilicone oils, etc.

Natural base oils include mineral lubricating oils which may vary widely as to their crude source, e.g., whether paraffinic, naphthenic, mixed, paraffinic-naphthenic, and the like; as well as to their formation, e.g., distillation range, straight run or cracked, hydrofined, solvent extracted and the like.

More specifically, the natural lubricating oil base stocks which can be used in the compositions of this invention may be straight mineral lubricating oil or distillates derived from paraffinic, naphthenic, asphaltic, or mixed base crudes, or, if desired, various blends of oils may be employed as well as residuals, particularly those from which asphaltic constituents have been removed. The oils may be refined by conventional methods using acid, alkali, and/or clay or other agents such as aluminum chloride, or they may be extracted oils produced, for example, by solvent extraction with solvents of the type of phenol, sulfur dioxide, furfural, dichlorodiethyl ether, nitrobenzene, crotonaldehyde, etc.

The lubricating oil base stock conveniently has a viscosity of typically about 2.5 to about 12, and preferably about 2.5 to about 9 cSt at 100° C.

Thus, the additives of the present invention can be employed in a hydrocarbon oil (i.e., fuel oil or lubricating oil) composition which comprises hydrocarbon oil, typically in a major amount, and the additive, typically in a minor amount, which is effective to impart or enhance one or more of the low temperature flow properties described herein. Additional conventional additives selected to meet the particular requirements of a selected type of hydrocarbon oil composition can be included as desired.

The additives of this invention are oil-soluble, dissolvable in oil with the aid of a suitable solvent, or are stably dispersible materials. Oil-soluble, dissolvable, or stably dispersible as that terminology is used herein does not necessarily indicate that the materials are soluble, dissolvable, miscible, or capable of being suspended in oil in all proportions. It does mean, however, that the additives, for instance, are soluble or stably dispersible in oil to an extent sufficient to exert their intended effect in the environment in which the oil is employed. Moreover, the additional incorporation of other additives may also permit incorporation of higher levels of a particular polymer adduct hereof, if desired.

Accordingly, while any effective amount of these additives can be incorporated into the fully formulated hydrocarbon oil composition, it is contemplated that such effective amount be sufficient to provide said hydrocarbon oil composition with an amount of the additive of typically from 0.005 to 10, e.g., 0.01 to 2, and preferably from 0.025 to 0.25 wt. %, based on the weight of said composition.

The additives of the present invention can be incorporated into the hydrocarbon oil in any convenient way. Thus, they can be added directly to the oil by dispersing, or dissolving the same in the oil at the desired level of concentration, typically with the aid of a suitable solvent such as toluene, cyclohexane, or tetrahydrofuran. Such blending can occur at room temperature or elevated temperatures. In this form the additive per se is thus being utilized as a 100% active ingredient form which can be added to the oil or fuel formulation by the purchaser. Alternatively, these additives may be blended with a suitable oil-soluble solvent and/or base oil to form a concentrate, which may then be blended with a hydrocarbon oil base stock to obtain the final formulation. Concentrates will typically contain from about 1 to 50%, by weight of the additive, and preferably from about 10 to 30% by weight of the additive.

The hydrocarbon oil base stock for the additives prepared as disclosed in this invention typically is adapted to perform a selected function by the incorporation of additives therein to form lubricating oil compositions (i.e., formulations).

Representative additives typically present in such formulations include viscosity modifiers, corrosion inhibitors, oxidation inhibitors, friction modifiers, dispersants, anti-foaming agents, anti-wear agents, pour point depressants, detergents, rust inhibitors and the like.

Viscosity modifiers, or viscosity index (V.I.) improvers impart high and low temperature operability to the lubricating oil and permit it to remain shear stable at elevated temperatures and also exhibit acceptable viscosity or fluidity at low temperatures. These viscosity index improvers are generally high molecular weight hydrocarbon polymers including polyesters. The V.I. improvers may also be derivatized to include other properties or functions, such as the addition of dispersancy properties.

These oil soluble V.I. polymers will generally have number average molecular weights of from about 40,000 to 1,000,000, preferably from about 40,000 to about 300,000, as determined by gel permeation chromatography or membrane osmometry.

Examples of suitable hydrocarbon polymers include homopolymers and interpolymers of two or more monomers of $C_2$ to $C_{30}$, e.g., $C_2$ to $C_8$ olefins, including both alpha-olefins and internal olefins, which may be straight or branched, aliphatic, aromatic, alkyl-aromatic, cycloaliphatic, etc. Frequently they will be of ethylene with $C_3$ to $C_{30}$ olefins, particularly preferred being the copolymers of ethylene and propylene. Other polymers can be used such as polyisobutylenes, homopolymers and interpolymers of $C_6$ and higher alpha-olefins, atactic polypropylene, hydrogenated polymers and copolymers and terpolymers of styrene, e.g., with isoprene and/or butadiene.

More specifically, other hydrocarbon polymers suitable as viscosity index improvers include those which may be described as hydrogenated or partially hydrogenated homopolymers, and random, tapered, star, or block interpolymers (including terpolymers, tetrapolymers, etc.) of conjugated dienes and/or monovinyl aromatic compounds with, optionally, alpha-olefins or lower alkenes, e.g., $C_3$ to $C_{18}$ alpha-olefins or lower alkenes. The conjugated dienes include isoprene, butadiene, 2,3-dimethylbutadiene, piperylene and/or mixtures thereof, such as isoprene and butadiene. The monovinyl aromatic compounds include any of the following, or mixtures thereof, vinyl di- or polyaromatic compounds, e.g., vinyl naphthalene, but are preferably monovinyl monoaromatic compounds, such as styrene or alkylated styrenes substituted at the alpha-carbon atoms of the styrene, such as alpha-methylstyrene, or at ring carbons, such as o-, m-, p-methylstyrene, ethylstyrene, propylstyrene, isopropyl-styrene, butylstyrene, isobutylstyrene, tert-butylstyrene (e.g., p-tertbutylstyrene). Also included are vinylxylenes, methylethyl styrenes and ethylvinylstyrenes. Alpha-olefins and lower alkenes optionally included in these random, tapered and block copolymers preferably include ethylene, propylene, butene, ethylene-propylene copolymers, isobutylene, and polymers and copolymers thereof. As is also known in the art, these random, tapered and block copolymers may include relatively small amounts, that is less than about 5 moles, of other copolymerizable monomers such as vinyl pyridines, vinyl lactams, methacrylates, vinyl chloride, vinylidene chloride, vinyl acetate, vinyl stearate, and the like.

Specific examples include random polymers of butadiene and/or isoprene and polymers of isoprene and/or butadiene and styrene. Typical block copolymers include polystyrene-polyisoprene, polystyrene-polybutadiene, polystyrene-polyethylene, polystyrene-ethylene propylene copolymer, polyvinyl cyclohexane-hydrogenated polyisoprene, and polyvinyl cyclohexane-hydrogenated polybutadiene. Tapered polymers include those of the foregoing monomers prepared by methods known in the art. Star-shaped polymers typically comprise a nucleus and polymeric arms linked to said nucleus, the arms being comprised of homopolymer or interpolymer of said conjugated diene and/or monovinyl aromatic monomers. Typically, at least about 80% of the aliphatic unsaturation and about 20% of the aromatic unsaturation of the star-shaped polymer is reduced by hydrogenation.

Representative examples of patents which disclose such hydrogenated polymers or interpolymers include U.S. Pat. Nos. 3,312,621; 3,318,813; 3,630,905; 3,668,125; 3,763,044; 3,795,615; 3,835,053; 3,838,049; 3,965,019; 4,358,565; and 4,557,849, the disclosures of which are herein incorporated by reference.

The polymer may be degraded in molecular weight, for example by mastication, extrusion, oxidation or thermal degradation, and it may be oxidized and contain oxygen. Also included are derivatized polymers such as post-grafted interpolymers of ethylene-propylene with an active monomer such as maleic anhydride which may be further reacted with an alcohol, or amine, e.g., an alkylene polyamine or hydroxy amine, e.g., see U.S. Pat. Nos. 4,089,794; 4,160,739; 4,137,185; or copolymers of ethylene and propylene reacted or grafted with nitrogen compounds such as shown in U.S. Pat. Nos. 4,068,056; 4,068,058; 4,146,489; and 4,149,984.

Suitable hydrocarbon polymers are ethylene interpolymers containing from 15 to 90 wt. % ethylene, preferably 30 to 80 wt. % of ethylene and 10 to 85 wt. %, preferably 20 to 70 wt. % of one or more $C_3$ to $C_8$, alpha-olefins. While not essential, such interpolymers preferably have a degree of crystallinity of less than 10 wt. %, as determined by X-ray and differential scanning calorimetry. Copolymers of ethylene and propylene are most preferred. Other alpha-olefins suitable in place of propylene to form the copolymer, or to be used in combination with ethylene and propylene, to form a terpolymer, tetrapolymer, etc., include 1-butene, 1-pentene, 1-hexene, 1-heptene, 1-octene, etc.; also branched chain alpha-olefins, such as 4-methyl-1-pentene, 4-methyl-1-hexene, 5-methyl-1-pentene, 4,4-dimethyl-1-pentene, and 6-methyl-1-heptene, etc., and mixtures thereof.

Terpolymers, tetrapolymers, etc., of ethylene, said $C_{3-8}$ alpha-olefin, and a non-conjugated diolefin or mixtures of such diolefins may also be used. The amount of the non-conjugated diolefin generally ranges from about 0.5 to 20 mole percent, preferably from about 1 to about 7 mole percent, based on the total amount of ethylene and alpha-olefin present.

Corrosion inhibitors, also known as anti-corrosive agents, reduce the degradation of the metallic parts contacted by the lubricating oil composition. Illustrative of corrosion inhibitors are phosphosulfurized hydrocarbons and the products obtained by reaction of a phosphosulfurized hydrocarbon with an alkaline earth metal oxide or hydroxide, preferably in the presence of an alkylated phenol or of an alkylphenol thioester, and also preferably in the presence of carbon dioxide. Phosphosulfurized hydrocarbons are prepared by reacting a suitable hydrocarbon such as a terpene, a heavy petroleum fraction of a $C_2$ to $C_6$ olefin polymer such as polyisobutylene, with from 5 to 30 wt. % of a sulfide of phosphorus for ½ to 15 hours, at a temperature in the range of about 66° to about 316° C. Neutralization of the phosphosulfurized hydrocarbon may be effected in the manner taught in U.S. Pat. No. 1,969,324.

Oxidation inhibitors, or antioxidants, reduce the tendency of mineral oils to deteriorate in service which deterioration can be evidenced by the products of oxidation such as sludge and varnish-like deposits on the metal surfaces, and by viscosity growth. Such oxidation inhibitors include alkaline earth metal salts of alkylphenolthioesters having preferably $C_5$ to $C_{12}$ alkyl side chains, e.g., calcium nonylphenol sulfide, barium t-octylphenyl sulfide, dioctylphenylamine, phenylalphanaphthylamine, phospho- sulfurized or sulfurized hydrocarbons, etc.

Other oxidation inhibitors or antioxidants useful in this invention comprise oil-soluble copper compounds. The copper may be blended into the oil as any suitable oil-soluble copper compound. By oil soluble it is meant that the compound is oil soluble under normal blending conditions in the oil or additive package. The copper compound may be in the cuprous or cupric form. The copper may be in the form of the copper dihydrocarbyl thio- or dithio-phosphates. Alternatively, the copper may be added as the copper salt of a synthetic or natural carboxylic acid. Examples of same thus include $C_{10}$ to $C_{18}$ fatty acids, such as stearic or palmitic acid, but unsaturated acids such as oleic or branched carboxylic acids such as napthenic acids of molecular weights of from about 200 to 500, or synthetic carboxylic acids, are preferred, because of the improved handling and solubility properties of the resulting copper carboxylates. Also useful are oil-soluble copper dithiocarbamates of the general formula (RR'NCSS)nCu (where n is or 2 and R and R' are the same or different hydrocarbyl radicals containing from 1 to 18, and preferably 2 to 12, carbon atoms, and including radicals such as alkyl, alkenyl, aryl, arylalkyl, alkaryl and cycloaliphatic radicals. Particularly preferred as R and R' groups are alkyl groups of from 2 to 8 carbon atoms. Thus, the radicals may, for example, be ethyl, n-propyl, i-propyl, n-butyl, i-butyl, sec-butyl, amyl, n-hexyl, i-hexyl, n-heptyl, n-octyl, decyl, dodecyl, octadecyl, 2-ethylhexyl, phenyl, butylphenyl, cyclohexyl, methylcyclopentyl, propenyl, butenyl, etc. In order to obtain oil solubility, the total number of carbon atoms (i.e., R and R') will generally be about 5 or greater. Copper sulphonates, phenates, and acetylacetonates may also be used.

Exemplary of useful copper compounds are copper CuI and/or CuII salts of alkenyl succinic acids or anhydrides. The salts themselves may be basic, neutral or acidic. They may be formed by reacting (a) polyalkylene succinimides (having polymer groups of $M_n$ of 700 to 5,000) derived from polyalkylene-polyamines, which have at least one free carboxylic acid group, with (b) a reactive metal compound. Suitable reactive metal compounds include those such as cupric or cuprous hydroxides, oxides, acetates, borates, and carbonates or basic copper carbonate.

Examples of these metal salts are Cu salts of polyisobutenyl succinic anhydride, and Cu salts of polyisobutenyl succinic acid. Preferably, the selected metal employed is its divalent form, e.g., Cu+2. The preferred substrates are polyalkenyl succinic acids in which the alkenyl group has a molecular weight greater than about 700. The alkenyl group desirably has a $M_n$ from about 900 to 1,400, and up to 2,500, with a $M_n$ of about 950 being most preferred. Especially preferred is polyisobutylene succinic anhydride or acid. These materials may desirably be dissolved in a solvent, such as a mineral oil, and heated in the presence of a water solution (or slurry) of the metal bearing material. Heating may take place between 70° and about 200° C. Temperatures of 110° C. to 140° C. are entirely adequate. It may be necessary, depending upon the salt produced, not to allow the reaction to remain at a temperature above about 140° C. for an extended period of time, e.g., longer than 5 hours, or decomposition of the salt may occur.

The copper antioxidants (e.g., Cu-polyisobutenyl succinic anhydride, Cu-oleate, or mixtures thereof) will be generally employed in an amount of from about 50 to 500 ppm by weight of the metal, in the final lubricating or fuel composition.

Friction modifiers serve to impart the proper friction characteristics to lubricating oil compositions such as automatic transmission fluids.

Representative examples of suitable friction modifiers are found in U.S. Pat. No. 3,933,659 which discloses fatty acid esters, amides, and tertiary amines, e.g., hydroxyamines; U.S. Pat. No. 4,176,074 which describes molybdenum complexes of polyisobutenyl succinic anhydride-amino alkanols; U.S. Pat. No. 4,105,571 which discloses glycerol esters of dimerized fatty acids; U.S. Pat. No. 3,779,928 which discloses alkane phosphonic acid salts; U.S. Pat. No. 3,778,375 which discloses reaction products of a phosphonate with an oleamide; U.S. Pat. No. 3,852,205 which discloses S-carboxyalkylene hydrocarbyl succinimide, S-carboxyalkylene hydrocarbyl succinamic acid and mixtures thereof; U.S. Pat. No. 3,879,306 which discloses N-(hydroxyalkyl)alkenyl-succinamic acids or succinimides; U.S. Pat. No. 3,932,290 which discloses reaction products of di-(lower alkyl) phosphites and epoxides; and U.S. Pat. No. 4,028,258 which discloses the alkylene oxide adduct of phosphosulfurized N-(hydroxyalkyl) alkenyl succinimides; and succinate esters, or metal salts thereof, of hydrocarbyl substituted succinic acids or anhydrides and thiobis-alkanols such as described in U.S. Pat. No. 4,344,853. The disclosures of the above references are herein incorporated by reference.

Dispersants maintain oil insolubles, resulting from oxidation during use, in suspension in the fluid thus preventing sludge flocculation and precipitation or deposition on metal parts. Suitable dispersants include high molecular weight alkyl succinimides, the reaction product of oil-soluble polyisobutylene succinic anhydride with ethylene amines such as tetraethylene pentamine and borated salts thereof.

Pour point depressants, otherwise known as lube oil flow improvers, lower the temperature at which the fluid will flow or can be poured. Such additives are well known. Typical of those additives which usefully optimize the low temperature fluidity of the fluid are $C_8$-$C_{18}$ dialkylfumarate vinyl acetate copolymers, polymethacrylates, and wax naphthalene.

Foam control can be provided by an antifoamant of the polysiloxane type, e.g., silicone oil and polydimethyl siloxane.

Anti-wear agents, as their name implies, reduce wear of metal parts. Representatives of conventional anti-wear agents are zinc dialkyldithiophosphate and zinc diaryldithiosphate.

Detergents and metal rust inhibitors include the metal salts of sulphonic acids, alkyl phenols, sulfurized alkyl phenols, alkyl salicylates, naphthenates and other oil-soluble mono- and di-carboxylic acids. Highly basic (viz, overbased) metal salts, such as highly basic alkaline earth metal sulfonates (especially Ca and Mg salts) are frequently used as detergents. Representative examples of such materials, and their methods of preparation, are found in U.S. Pat. No. 4,863,624, the disclosure of which is hereby incorporated by reference.

Some of these numerous additives can provide a multiplicity of effects, e.g., a dispersant-oxidation inhibitor. This approach is well known and need not be further elaborated herein.

Compositions when containing these conventional additives are typically blended into the base oil in amounts which are effective to provide their normal attendant function. Representative effective amounts of such additives are illustrated as follows:

| Additive | Wt. % a.i. (Broad) | Wt. % a.i. (Preferred) |
|---|---|---|
| Viscosity Modifier | .01–12 | .01–4 |
| Corrosion Inhibitor | 0.01–5 | .01–1.5 |
| Oxidation Inhibitor | 0.01–5 | .01–1.5 |
| Dispersant | 0.1–20 | 0.1–8 |
| Pour Point Depressant | 0.005–10 | .01–2 |
| Anti-Foaming Agents | 0.001–3 | .001–0.15 |
| Anti-Wear Agents | 0.001–5 | .001–1.5 |
| Friction Modifiers | 0.01–5 | .01–1.5 |
| Detergents/Rust Inhibitors | .01–10 | .01–3 |
| Mineral Oil Base | Balance | Balance |

When other additives are employed, it may be desirable, although not necessary, to prepare additive concentrates comprising concentrated solutions or dispersions of the flow improver (in concentrate amounts hereinabove described), together with one or more of said other additives (said concentrate when constituting an additive mixture being referred to herein as an additive-package) whereby several additives can be added simultaneously to the base oil to form the hydrocarbon oil composition. Dissolution of the additive concentrate into the hydrocarbon oil may be facilitated by solvents and by mixing accompanied with mild heating, but this is not essential. The concentrate or additive-package will typically be formulated to contain the flow improver additive and optional additional additives in proper amounts to provide the desired concentration in the final formulation when the additive-package is combined with a predetermined amount of base hydrocarbon oil. Thus, the product produced by the process of the present invention can be added to small amounts of base oil or other compatible solvents along with other desirable additives to form additive-packages containing active ingredients in collective amounts of typically from about 2.5 to about 90%, and preferably from about 5 to about 75%, and most preferably from about 8 to about 50% by weight additives in the appropriate proportions with the remainder being base oil. For safety considerations, the base oil for concentrates is typically a lubricating oil rather than a fuel oil.

The final formulations may employ typically about 10 wt. % of the additive-package with the remainder being base oil.

All of said weight percents expressed herein are based on active ingredient (a.i.) content of the additive, and/or upon the total weight of any additive-package, or formulation which will be the sum of the a.i. weight of each additive plus the weight of total oil or diluent.

This invention will be further understood by reference to the following examples, wherein all parts are parts by weight and all molecular weights are either number average molecular weight determined by vapor-phase osmometry or weight average molecular weights determined by gel permeation chromatography as noted unless otherwise specified, and which include preferred embodiments of the invention.

The following examples are given as specific illustrations of the claimed invention. It should be understood, however, that the invention is not limited to the specific details set forth in the examples. All parts and percentages in the examples, as well as in the remainder of the specification, are by weight unless otherwise specified.

EXAMPLE 1

This example is directed to the preparation of a typical alkylated phenol component using the process disclosed in U.S. Pat. No. 4,976,882 and alkyl phenol-sulfur condensates produced thereby. Octadecyl phenol was prepared by charging into a four-neck, 5-liter round bottom flask equipped with a mechanical stirrer, 933 grams of phenol (9.93 moles) and 286 grams of Amberlyst 15 catalyst. A reflux condenser, a thermometer, an addition funnel, and a nitrogen inlet tube were attached to the flask and the mixture was heated to 70° C. With stirring under a blanket of nitrogen, 834 grams (3.31 moles) of 1-octadecene was added dropwise over a period of about one hour. The temperature was raised to 90° C and maintained at this temperature for four hours. The reaction mixture was then cooled to 50° C. and filtered to remove the catalyst. The excess phenol was removed by vacuum distillation. The yield was 1,008 grams or 88%. The product has a refractive index of 1.4859 at 25° C., a viscosity of 38.0 cP at 40° C., and a hydroxyl number of 144 mg KOH/g. The infrared spectrum of the product showed absorption bands at 830 and 750 cm$^{-1}$m which are characteristic of alkyl phenols. The aromatic substitution pattern was determined by $^{13}$C-NMR spectroscopy and showed that the ortho to para ratio was 2.0:1.0. The alkyl substitution pattern was determined by $^1$H-NMR spectroscopy and showed that the product consisted of 50 mole % 2-substituted alkylate and 50 mole % ≧ 3-substituted alkylate.

EXAMPLE 2

In order to demonstrate the criticality of the linearity of the alkyl group used in the alkyl phenolformaldehyde condensates, Example was repeated, except that in this case the mixture was heated to 115° C. instead of 90° C. The yield of octadecyl phenol was 893 grams, or 78%. The product had a hydroxyl number of 138 mg KOH/g, and its infrared spectrum showed absorptions at 830 and 750 cm$^{-1}$, which are characteristic of alkyl phenols. The aromatic substitution pattern was determined by $^{13}$C-NMR spectroscopy and showed that the ortho to para ratio was 1.8:1.0. The alkyl substitution pattern was determined by the $^1$H-NMR spectroscopy and showed that the product consisted of 35 mole % 2-substituted alkylate and 65 mole % ≧ 3-alkylate. The greater degree of rearrangement in this alkyl phenol was due to the higher reaction temperature.

EXAMPLE 3

In order to demonstrate the method of the present invention to produce alkyl phenols with a less rearrangement, Example 1 was repeated, except that a dipolar aprotic cosolvent, nitrobenzene, was added to the reaction mixture. Into a four-neck 1-liter round-bottom flask equipped with a mechanical stirrer, 125 grams of phenol (1.33 moles), 31.5 grams of Amberlyst 15 catalyst, and 164 grams of nitrobenzene were charged. A reflux condenser, a thermometer, an addition funnel and a nitrogen inlet tube were attached to the flask and the mixture was heated to 70° C. With stirring under a blanket of nitrogen, 109 grams (0.43 moles) of 1-octadecene was added dropwise over a period of about one hour. The temperature was raised to 90° C. and maintained at this temperature for four hours. The reaction mixture was then cooled to 50° C. and filtered to remove the catalyst. The excess phenol and nitrobenzene were removed by vacuum distillation. The yield was 207 grams, or 99%. The infrared spectrum of the product showed absorption bands at 830 and 750 cm$^{-1}$, which are characteristic of alkyl phenols. The aromatic substitution pattern was determined by $^{13}$C-NMR spectroscopy and showed that the ortho to para ratio was 1.7:1.0. The alkyl substitution pattern was determined by $^1$H-NMR spectroscopy and showed that the product consisted of 59 mole % 2-substituted alkylate and 41 mole % ≧ 3-substituted alkylate, i.e., 18% less rearrangement than the alkylate produced in accordance with Example 1.

EXAMPLE 4

As an example of the preparation of an alkylated phenol-sulfur condensate polymer of the present invention, into a four-necked, 1 liter round bottom flask, equipped with a mechanical stirrer, a thermometer, addition funnel, nitrogen inlet tube, and a Dean-Stark trap with a reflux condenser, were charged 250 grams of octadecyl phenol produced in accordance with Example 1. The octadecyl phenol was heated to 80° C. While stirring, 82 grams of a mixture of 76% sulfur dichloride and 24% sulfur monochloride were added over a period of about one hour, with the temperature maintained at about 80 C. After the addition was completed, the reaction mixture was soaked for about 5 minutes at 80° C. and then heated to 95° C. and sparged with nitrogen for one hour. While continuing stirring, 107 grams of diluent oil were added, and the mixture was stirred for 15 minutes and cooled to room temperature. The product had a sulfur content of 7.50%. The number average molecular weight (VPO) of this polymer was 4,900, and its weight average molecular weight (GPC) was 11,000.

EXAMPLE 5

As another example of the preparation of an alkyl phenol-sulfur condensate polymer, Example 4 was repeated, except that the octadecyl phenol produced in accordance with Example 2 was used. The sulfur content of the product was 7.42%. The number average and weight average molecular weights of the dialyzed polymer by gel permeation chromatography were 4,400 and 10,100, respectively.

EXAMPLE 6

As another example of the preparation of an alkyl phenol-sulfur condensate polymer, Example 4 was repeated, except that the octadecyl phenol produced in accordance with Example 3 was used. The sulfur content of the product was 7.48%. The number average and weight average molecular weights of the polymer were 4,800 and 9,300, respectively.

EXAMPLE 7

In order to demonstrate the criticality of the linearity of the alkyl groups used in the alkyl phenol-sulfur condensates, the octadecyl phenol-sulfur condensates produced in accordance with Examples 4-6 were tested for pour point depressancy in a lube base stock (Exxon S150N). Pour points were measured according to ASTM D 97 method, and the results are set forth in Table 1 below. These results demonstrate that: (1) the 15-mole % reduction in alkylate containing a pendant method group on the 2-carbon and a corresponding increase in alkylate having substitution on the 3- or higher carbon decreases pour point depressancy significantly (compare runs 1, 2 and 5); (2) the 9-mole % increase in alkylate containing a pendant method group on the 2-carbon and a corresponding decrease in the alkylate having substitution on the 3- or higher carbon increased pour point depressancy significantly (compare runs 1, 3 and 9).

The decreased pour point depressancy of the octadecyl phenol-sulfur condensate produced in accordance with Example 5, compared with Example 4, is because of the greater degree of rearrangement in the alkylate used, i.e., Example 2. This results from a higher reaction temperature.

The increased pour point depressancy of the octadecyl phenol-sulfur condensate produced in accordance with Example 6, compared to Example 4, is because of less rearrangement in the alkylate used, i.e., Example 3. This results from the use of the dipolar aprotic cosolvent, nitrobenzene.

TABLE 1
POUR POINT DEPRESSANCY OF OCTADECYL PHENOL-SULFUR CONDENSATES WITH VARYING DEGREES OF ALKYLATE REARRANGEMENT

| Run | Additive | Additive Conc. (Wt %) | 2-Substituted Alkylate (5) | Pour Point (°F.) | | |
|---|---|---|---|---|---|---|
| 1 | Nil | 0.00 | — | +10, | +15, | +15 |
| 2 | Example 4 | 0.05 | 50 | −15, | −15, | −10 |
| 3 | Example 4 | 0.10 | 50 | −25, | −25, | −20 |
| 4 | Example 4 | 0.20 | 50 | −40, | −40, | −35 |
| 5 | Example 5 | 0.05 | 35 | +10, | +10, | +15 |
| 6 | Example 5 | 0.10 | 35 | −15, | −15, | −10 |
| 7 | Example 5 | 0.20 | 35 | −20, | −20, | −20 |
| 8 | Example 6 | 0.05 | 59 | −20, | −20, | −15 |
| 9 | Example 6 | 0.10 | 59 | −40, | −40, | −35 |
| 10 | Example 6 | 0.20 | 59 | −40, | −40, | −40 |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for producing a polymeric additive suitable for improving the low temperature flow properties and oxidative stability of hydrocarbon oil which comprises (1) producing alkylated phenol, comprising at least 80 mole percent difunctional alkylated phenol, derived by reacting (a) phenol and (b) linear alpha-olefin having (i) from 6 to 50 carbon atoms, (ii) an average carbon number of from about 12 to 26; and (iii) not more than about 10 mole percent containing less than 12 carbon atoms and not more than about 10 mole percent containing more than 26 carbon atoms, said alkylation being conducted in the presence of a dipolar aprotic cosolvent in a manner and under conditions sufficient to render the alkyl groups of said alkylated phenol essentially linear; and (2) condensing said alkylated phenol consisting essentially of alkylated phenol produced in accordance with step (1) with a sulfurizing agent to produce sulfur bridged condensate of said alkylated phenol and said sulfurizing agent having a number average molecular weight of at least about 3,000 and molecular weight distribution of at least about 1.5.

2. The method of claim 1 wherein said sulfurizing agent is selected from the group consisting of elemental sulfur and sulfur-containing compounds having the formula $S_xCl_2$, wherein x is an integer from 1 to 2.

3. The method of claim 1 wherein said condensing step is conducted in the further presence of at least one comonomer represented by the formula selected from the group consisting of:

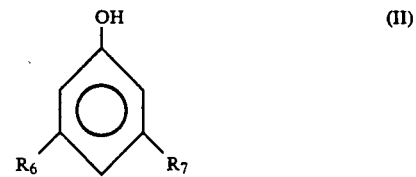

and:

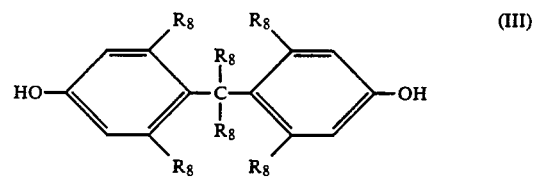

wherein $R_6$, $R_7$ and $R_8$ are each independently selected from the group consisting of hydrogen, alkyl, aryl, alkoxy, aryloxy, alkyl mercapto, and halogen, and wherein said comonomer is present in an amount of less than about 10 wt. of said combination of said alkylated phenol and said sulfurizing agent.

4. The method of claim 1 wherein said linear alpha-olefin comprises a mixture of linear alpha-olefins.

5. The method of claim 1 wherein the dipolar-aprotic solvent has a dielectric constant of greater than about 10.

6. The method of claim 5 wherein the dipolar-aprotic solvent has a dielectric constant of greater than about 20.

7. The method of claim 6 wherein the dielectric constant of the dipolar-aprotic cosolvent ranges from about 20 to about 50.

8. The method of claim 1 wherein the dipolar-aprotic solvent is selected from the group consisting of nitrobenzene; nitromethane; N,N-dimethylformamide; acetonitrile, sulfolane, dimethyl sulfoxide.

9. The method of claim 8 wherein the dipolar-aprotic solvent is nitrobenzene.

10. The method of claim 1 wherein the linear alpha-olefins comprise olefins having from $C_4$ to $C_{50}$ carbon atoms.

11. The method of claim 10 wherein the olefins have average carbon atom numbers between 12 and 26.

12. The method of claim 11 wherein said alpha-olefins have average carbon atom numbers between 18 and 20.

13. The method of claim 1 wherein the alkylation is conducted at a temperature of from about 50° C. to about 200° C.

14. The method of claim 13 wherein the alkylation is conducted below 100° C.

15. The method of claim 14 wherein the alkylation is conducted at a temperature of from 50° C. to 90° C.

16. The method of claim 1 wherein the molar ratio of phenol to olefin ranges from 2:1 to 10:1.

17. The method of claim 16 wherein the molar ratio of phenol to olefin is from about 2:1 to 5:1.

18. The method of claim 1, 4, 15 or 17 wherein said alkylation is conducted in the presence of an acidic crystalline aluminasilicate zeolite catalyst in order to minimize the production of dialkylate therein.

19. The method of claim 18 wherein the alkylation is conducted in the presence of a zeolite catalyst having a silica to alumina molar ratio of from about 3:1 to about 6:1.

20. The method of claim 19 wherein the alkylation is conducted in the presence of a zeolite catalyst having a surface area of at least about 625 $m^2/g$.

21. The method of claim 20 wherein said zeolite catalyst has a free pore diameter of between about 6 A and about 8A.

22. The method of claim 21 wherein said alkylation is conducted using a molar ratio of said phenol to said linear alpha-olefin of less than about 2:1.

23. The method of claim 18 wherein said alkylation is conducted using a molar ratio of said phenol to said linear alpha-olefin of between about 1.7:1 and about 1:1.

* * * * *